United States Patent [19]

Maffrand

[11] 4,076,819
[45] Feb. 28, 1978

[54] THIENO-PYRIDINE DERIVATIVES AND THERAPEUTIC COMPOSITION CONTAINING SAME

[75] Inventor: Jean-Pierre Maffrand, Toulouse, France

[73] Assignee: Parcor, Paris, France

[21] Appl. No.: 676,796

[22] Filed: Apr. 14, 1976

[30] Foreign Application Priority Data

May 30, 1975 France .................................. 75 17007

[51] Int. Cl.$^2$ ..................... A61K 31/44; C07D 407/04
[52] U.S. Cl. ............................... 424/256; 260/294.8 C
[58] Field of Search .................. 260/294.8 C; 424/256

[56] References Cited

U.S. PATENT DOCUMENTS

3,983,125   9/1976   Amselem ...................... 260/294.8 C

OTHER PUBLICATIONS

Burger, Medicinal Chemistry, Second Edition, Interscience Publishers, p. 497, (1960).

*Primary Examiner*—Alan L. Rotman
*Attorney, Agent, or Firm*—Young & Thompson

[57] ABSTRACT

This invention relates to thieno-pyridine derivatives having the formula:

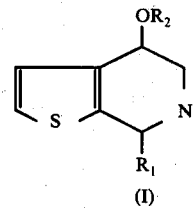

or 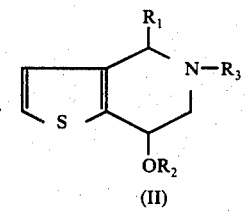

(I)                                     (II)

in which $R_1$ is hydrogen or alkyl having 1-6 carbon atoms; $R_2$ is hydrogen or acetyl or lower alkylcarbamoyl and $R_3$ is methyl, nitrobenzyl, chlorobenzyl, methoxybenzyl, chlorobenzoyl, trimethoxybenzoyl, pyrrolidinoacetyl, p.toluene-sulfonyl, phenylcarbamoyl, phenylthiocarbamoyl, 3-oxo-butyl, lower alkyl-carbamoyloxy, phenethyl, dichloroacetyl, 2-chlorophenoxy-2-methyl-propionyl or chlorophenyl-carbamoyl, and their pharmaceutically acceptable acid addition salts.

Said derivatives have useful anti-inflammatory properties and inhibiting effects on blood plate aggregation which make them therapeutically valuable.

4 Claims, No Drawings

THIENO-PYRIDINE DERIVATIVES AND THERAPEUTIC COMPOSITION CONTAINING SAME

This invention relates to new thieno-pyridine derivatives, therapeutic compositions for and to their application in human and veterinary medicine.

The new compounds of this invention have one or the other of the following formulae:

(I) (II)

in which $R_1$ represents hydrogen or an alkyl group having 1–6 carbon atoms; $R_2$ represents hydrogen or acetyl or lower alkyl-carbamoyl; and $R_3$ represents methyl, nitrobenzyl, chlorobenzyl, methoxybenzyl, chlorobenzoyl, trimethoxybenzoyl, pyrrolidinoacetyl, p.toluene-sulfonyl, phenylcarbamoyl, phenylthiocarbamoyl, 3-oxo-butyl, lower alkyl-carbamoyloxy, phenethyl, dichloroacetyl, 2-chlorophenoxy-2-methyl-propionyl or chlorophenyl-carbamoyl.

The invention includes also within its scope the pharmaceutically acceptable acid addition salts with inorganic or organic acids.

The acid addition salts and the quaternary ammonium derivatives of the derivatives of the formulae (I) and (II) are prepared by conventional methods well known by those expert in the art.

The following non-limiting Examples are given to illustrate the preparation of the compounds of this invention.

EXAMPLE 1

7-Hydroxy-5-p.nitrobenzyl-4,5,6,7-tetrahydro-thieno[3,2-c]-pyridine (Derivative 1; Procedure (a))

A mixture of 7-hydroxy-4,5,6,7-tetrahydro-thieno[3,2-c]-pyridine hydrochloride (7 g; 36.52 mmoles), p-nitrobenzyl chloride (6.26 g; 36.52 mmoles), potassium carbonate (10.18 g) and ethanol (60 cc) is refluxed during 1.5 hours. After filtration of the inorganic salts, the filtrate is concentrated in vacuo. The residue is dissolved in chloroform and the organic phase is washed with water, dried over sodium sulfate, filtered and concentrated in vacuo. The resulting oil is converted to the hydrochloride which is then recrystallized from 80% ethanol (M.p. = 200°–210° C (dec.); yield: 52%).

EXAMPLE 2

4-Hydroxy-6-pyrrolidinoacetyl-4,5,6,7-tetrahydro-thieno[2,3-c]-pyridine (Derivative 2; Procedure (b))

To a vigorously stirred mixture of 4-hydroxy-4,5,6,7-tetrahydro-thieno[2,3-c]-pyridine hydrochloride (12.35 g; 64.5 mmoles), sodium carbonate (13.7 g), water (50 cc) and chloroform (150 cc), is added dropwise a solution of chloroacetyl chloride (7.3 g; 64.5 mmoles) in chloroform (50 cc). The mixture is stirred 2 hours at room temperature, after which the organic phase is decanted, washed with water, dried over sodium sulfate, filtered and concentrated in vacuo. The residual oil is crystallized from isopropyl ether. The resulting crystals (M.p. = 103° C; yield: 72%) may be recrystallized from isopropanol-isopropyl ether (M.p. 107° C).

A mixture of the above product (9 g; 39 mmoles), pyrrolidine (2.8 g; 39 mmoles) and potassium carbonate (5.4 g) in dimethylformamide (50 cc) is heated during 3 hours at 100° C. After filtration of the inorganic salts, the filtrate is concentrated in vacuo. The residue is dissolved in methylene chloride, and the organic phase is then washed with water, dried over sodium sulfate, filtered and concentrated in vacuo. The crystalline residue is recrystallized twice from ethyl acetate (M.p = 117° C; yield: 42.5%).

EXAMPLE 3

6-p.Chlorobenzoyl-4-hydroxy-4,5,6,7-tetrahydro-thieno[2,3-c]-pyridine (Derivative 3; Procedure (b))

To a vigorously stirred mixture of 4-hydroxy-4,5,6,7-tetrahydro-thieno[2,3-c]-pyridine hydrochloride (4.77 g; 25 mmoles), sodium carbonate (5.3 g), chloroform (25 cc), is added dropwise a solution of p-chlorobenzoyl chloride (4.4 g; 25 mmoles) in chloroform (25 cc). After stirring during 1 hour at room temperature, the organic phase is decanted, washed with water, dried over sodium sulfate, filtered and concentrated in vacuo. The residue is crystallized from isopropyl ether, filtered and recrystallized from isopropanol (M.p. = 148° C; yield: 53%).

EXAMPLE 4

4-Hydroxy-6-p.toluenesulfonyl-4,5,6,7-tetrahydro-thieno[2,3-c]-pyridine (Derivative 4; Procedure (c))

To a vigorously stirred mixture of 4-hydroxy-4,5,6,7-tetrahydro-thieno[2,3-c]-pyridine hydrochloride (30 g; 0.156 moles), a saturated potassium carbonate solution (80 cc) and chloroform (200 cc) is added dropwise a solution of tosyl chloride (29.8 g; 0.156 moles) in chloroform (150 cc). After stirring 2 hours at room temperature, the organic phase is decanted, washed with water, dried over sodium sulfate and concentrated in vacuo. The residue is recrystallized from isopropanol (M.p. = 130° C; yield: 86%).

EXAMPLE 5

4-Hydroxy-6-N-phenylcarbamoyl-4,5,6,7-tetrahydro-thieno[2,3-c]-pyridine (Derivative 5; Procedure (d))

To a solution of 4-hydroxy-4,5,6,7-tetrahydro-thieno[2,3-c]-pyridine (5.6 g; 36.2 mmoles) in benzene (40 cc), is added dropwise a mixture of phenyl isocyanate (4.3 g; 36.2 mmoles) in benzene (10 ml). After stirring during 2 hours at room temperature, the resulting precipitate is filtered off, washed with ether and dried in vacuo. On recrystallization from ethanol, the desired product is obtained in a yield of 65% (M.p. = 200° C).

EXAMPLE 6

4-Hydroxy-6-N-phenylthiocarbamoyl-4,5,6,7-tetrahydro-thieno[2,3-c]-pyridine (Derivative 6; Procedure (d))

To a solution of 4-hydroxy-4,5,6,7-tetrahydro-thieno[2,3-c]-pyridine (5.8 g; 37.4 mmoles) in benzene (60 cc) and 95% ethanol (30 cc) is added dropwise a mixture of phenyl isothiocyanate (5.05 g; 37.4 mmoles) in benzene (20 cc). After stirring during 2.5 hours at room temperature, the resulting precipitate is filtered off, washed with ether and dried in vacuo (M.p. = 168° C; yield: 79%).

EXAMPLE 7

7-Hydroxy-5-(3-oxo-butyl)-4,5,6,7-tetrahydro-thieno[3,2-c]-pyridine (Derivative 7; Procedure (e) )

A mixture of 7-hydroxy-4,5,6,7-tetrahydro-thieno[3,2-c]-pyridine (5.7 g; 36.7 mmoles) and methyl vinyl ketone (2.6 g; 36.7 mmoles) in diethyl ether (10 cc) is stirred during 20 hours at room temperature. After concentration in vacuo, the residual oil is converted to the hydrochloride which is recrystallized from 95% ethanol (M.p. = 188°-190° C; yield: 65%).

EXAMPLE 8

7-Acetoxy-5-o-chlorobenzyl-4,5,6,7-tetrahydro-thieno[3,2-c]-pyridine (Derivative 8; Procedure (f))

A mixture of 7-hydroxy-5-o-chlorobenzyl-4,5,6,7-tetrahydro-[3,2-c]-pyridine (6.7 g; 24 mmoles), acetic anhydride (14 cc) and dry pyridine (40 cc) is stirred during 3 hours at room temperature. The mixture is then poured over ice, made alkaline with concentrated ammonia and extracted with ether. The organic extracts are washed with water, dried over sodium sulfate, filtered and concentrated in vacuo. The residual oil is converted to the hydrochloride which is recrystallized from ethanol-isopropanol (M.P. = 155°-165° C; Yield: 52.5%).

EXAMPLE 9

6-Methyl-4-N-propylcarbamoyloxy-4,5,6,7-tetrahydro-thieno-[2,3-c]-pyridine (Derivative 9; Procedure (g))

A mixture of 4-hydroxy-6-methyl-4,5,6,7-tetrahydro-thieno-[2,3-c]-pyridine (6 g; 35.4 mmoles), propyl isocyanate (3.9 g; 45.9 mmoles), triethylamine (3 g) and benzene (50 cc) is refluxed during 23 hours. The resulting material is concentrated in vacuo and the residue is dissolved in ether. The resulting solution is washed with water, dried over sodium sulfate, filtered and concentrated in vacuo. The residual oil is converted to the maleate (M.p. = 167° C; yield: 70.5%).

Using procedures analogous with those described above, the following compounds were prepared:

Derivative 10: 4-Hydroxy-6-methyl-4,5,6,7-tetrahydro-thieno[2,3-c]-pyridine, white crystals; M.p. = 94° C Derivative 11: 6,7-Dimethyl-4-hydroxy-4,5,6,7-tetrahydro-thieno-[2,3-c]-pyridine, maleate, cream-colored crystals; m.p. = 120° C.

Derivative 12: 4-Acetoxy-6-methyl-4,5,6,7-tetrahydro-thieno[2,3-c]-pyridine, maleate, pale cream-colored crystals; m.p. 141° C.

Derivative 13: 4-Acetoxy-6,6-dimethyl-4,5,6,7-tetrahydro-thieno-[2,3-c]-pyridinium iodide; white crystals; m.p. = 260°-262° C.

Derivative 14: 6-Methyl-4-N-methylcarbamoyloxy-4,5,6,7-tetrahydro-thieno[2,3-c]-pyridine, maleate semi-hydrate; white crystals; m.p. = 160° C Derivative 15: 4-N-Ethylcarbamoyloxy-6-methyl-4,5,6,7-tetrahydro-thieno[2,3-c]-pyridine, maleate semi-hydrate: white crystals; m.p. 144° C.

Derivative 16: 4-Hydroxy-6-(3-oxo-butyl)-4,5,6,7-tetrahydro-thieno[2,3-c]-pyridine; cream-colored crystals; m.p. 90° C.

Derivative 17: 4-Acetoxy-6-β-phenethyl-4,5,6,7-tetrahydro-thieno-[2,3-c]-pyridine, maleate; white crystals; m.p. 139° C.

Derivative 18: 4-Acetoxy-6-o-chlorobenzyl-4,5,6,7-tetrahydro-thieno[2,3-c]-pyridine, hydrochloride; grey crystals; m.p. = 145°-150° C.

Derivative 19: 6-o-Chlorobenzyl-4-hydroxy-7-methyl-4,5,6,7-tetrahydro-thieno[2,3-c]-pyridine, hydrochloride; white crystals; m.p. = 180°-183° C.

Derivative 20: 6-p-Chlorobenzyl-4-hydroxy-4,5,6,7-tetrahydro-thieno[2,3-c]-pyridine, maleate; creamy-white crystals; m.p. = 158° C.

Derivative 21: 4-Acetoxy-6-p-methoxybenzyl-4,5,6,7-tetrahydro-thieno[2,3-c]-pyridine, maleate; white crystals; m.p. = 162° C.

Derivative 22: 4-Hydroxy-6-o-nitrobenzyl-4,5,6,7-tetrahydro-thieno[2,3-c]-pyridine; hydrochloride; pale yellow crystals; m.p. = 180° C (decomposition).

Derivative 23: 4-Hydroxy-7-methyl-6-o-nitrobenzyl-4,5,6,7-tetrahydro-thieno[2,3-c]-pyridine; beige crystals; m.p. = 195° C (decomposition)

Derivative 24: 4-Hydroxy-6-p-nitrobenzyl-4,5,6,7-tetrahydro-thieno-[2,3-c]-pyridine, maleate; pale yellow crystals; m.p. = 175°-177° C.

Derivative 25: 4-Acetoxy-6-dichloroacetyl-4,5,6,7-tetrahydro-thieno-[2,3-c]-pyridine; white crystals; m.p. = 125° C.

Derivative 26: 4-Hydroxy-6-(3,4,5-trimethoxy-benzoyl)-4,5,6,7-tetrahydro-thieno[2,3-c]-pyridine; m.p. = 158° C.

Derivative 27: 6-(2-p-chlorophenoxy-2-methyl-propionyl)-4-hydroxy-4,5,6,7-tetrahydro-thieno[2,3-c]-pyridine; cream-colored material; m.p. = 127° C Derivative 28: 6-(N-p-Chlorophenylcarbamoyl)-4-hydroxy-4,5,6,7-tetrahydro-thieno[2,3-c]-pyridine; beige crystals; m.p. = 170° C.

Derivative 29: 7-Hydroxy-5-methyl-4,5,6,7-tetrahydro-thieno[3,2-c]-pyridine, maleate; white crystals; m.p. = 145° C.

Derivative 30: 5-o-Chlorobenzyl-7-hydroxy-4,5,6,7-tetrahydro-thieno[3,2-c]-pyridine, hydrochloride; white material; m.p. = 195°-215° C.

Derivative 31: 7-Hydroxy-5-o-nitrobenzyl-4,5,6,7-tetrahydro-thieno-[3,2-c]-pyridine, pale yellow crystals; m.p. = 125° C.

The results of toxicological and pharmacological tests reported below demonstrate the useful activities of the derivatives of this invention, particularly their vasodilatator activity and their inhibiting activity on blood plate aggregation.

Thus, the invention includes also within its scope a therapeutic composition having in particular an anti-inflammatory action, and an inhibiting activity on blood plate aggregation comprising, as active ingredient, an effective amount of a derivative of the formula (I) or (II) or a therapeutically acceptable acid addition salt thereof, and a therapeutically administrable carrier.

TOXICOLOGICAL INVESTIGATION

Said investigation demonstrated the low toxicity and the good tolerance of the derivatives of this invention.

For indicative purposes, the $LD_{50}/24$ hrs/kg body weight in mice, calculated according to the method of Miller and Tainter, by the intravenous route, is 90 mg for derivative 1, 225 mg for derivative 2, 260 mg for derivative 7, 200 mg for derivative 8, 220 mg for derivative 9, 340 mg for derivative 10, 220 mg for derivative 11, 260 mg for derivative 12, 280 mg for derivative 14, 270 mg for derivative 15, 250 mg for derivative 16, 110 mg for derivative 20, 245 mg for derivative 21, 150 mg for derivative 24 and 350 mg for derivative 29.

PHARMACOLOGICAL INVESTIGATION

The pharmacological tests demonstrate that the derivatives of this invention possess anti-inflammatory activities and an inhibiting activity on blood plate aggregation.

1. Anti-inflammatory action
(a) Localized carrageenin-induced edema method

A 1% carrageenin solution (1 ml) is injected in the metatarsal flexor muscles of the right hind limb of rats at time 0. The animals of the treated group are additionally administered orally 100 mg/kg of the test derivative, respectively 1 hour prior to and then simultaneously with the phlogogenic agent, and then one hour and 2.5 hours thereafter. The percent anti-inflammatory activity, as a function of time, is determined by measurements effected with a ROCH micrometer at times 0, 1 hour, 2 hours, 3 hours and 5 hours after carrageenin administration. The results obtained are given in following Table I:

TABLE I

| Derivative | Percent anti-inflammatory activity after 1 hour | after 2 hours | after 5 hours |
| --- | --- | --- | --- |
| 2 | 35 | 48 | 55 |
| 5 | 41 | 50 | 55 |
| 7 | 42 | 56 | 60 |
| 12 | 37 | 50 | 58 |
| 18 | 34 | 44 | 57 |
| 26 | 36 | 49 | 54 |
| 29 | 45 | 55 | 61 |

(b) Ovalbumin-induced systemic edema method

Rats are administered a simultaneous intraperitoneal injection of 1 ml ovalbumin and 0.5 ml of a 1% aqueous Evans Blue solution. The animals of the treated group are additionally administered orally 100 mg/kg of the test derivative, one hour prior to ovalbumin administration and simultaneously with said ovalbumin administration. The intensity of the phenomenon thus induced is scored according to a scale from 1 to 5, according to the progress of the inflammatory syndrome. The determinations are effected after 2 hours and after 3 hours. Thus are determined the mean intensity of the edema and the percent decrease of the edema reaction. The results obtained are given in following Table II:

TABLE II

| Derivative | Percent decrease After 2 hours | After 3 hours |
| --- | --- | --- |
| 2 | 38 | 44 |
| 5 | 33 | 43 |
| 7 | 41 | 52 |
| 12 | 46 | 59 |
| 18 | 42 | 58 |
| 26 | 51 | 63 |
| 29 | 49 | 59 |

2. Inhibiting activity on blood plate aggregation

Rat plasma, prepared to contain 600,000±20,000 blood platelets per $mm^3$ is normally cloudy. Addition of adenosine diphosphate induces blood plate aggregation and, thus, an increase of the light transmission, a phenomenon readily measurable with a spectrophotometer. When the same test is effected with a plasma prepared from the blood of an animal which has been administered 100 mg/kg of a derivative having an inhibiting effect on blood plate aggregation, there is no aggregation of the blood plates and the serum remains cloudy. The turbidimetric assay effected with a spectrophotometer provides a measure of the inhibiting activity on blood plate aggregation of the test derivatives.

The tests carried out with groups of five rats (three controls and two treated animals) show that the compounds of this invention induce a substantial percent inhibition on blood plate aggregation, said percent inhibition being respectively 92% for derivative 4, 89% for derivative 5, 86% for derivative 9, 88% for derivative 15, 74% for derivative 18, 93% for derivative 22, 84% for derivative 25 and 88% for derivative 29.

It is apparent from the toxicological and pharmacological investigations reported above, that the derivatives of this invention are endowed with a good tolerance and that they possess a valuable anti-inflammatory activity and a valuable inhibiting activity on blood plate aggregation.

The composition of this invention may be formulated, for oral administration, as tablets, coated tablets, capsules, drops or syrups. It may also be formulated as suppositories for rectal administration and as injectable solutions for parenteral administration.

Each unit dose contains advantageously 0.025–0.500 g active ingredient, the daily dosage regimen varying within a range from 0.025 g to 1 g active ingredient, according to the age of the patient and the severity of the condition to be treated.

Non-limiting Examples of pharmaceutical formulations of the composition of this invention are given below.

EXAMPLE 10

| Tablets | |
| --- | --- |
| Derivative n° 5 | 0.100 g |
| Starch | 0.025 g |
| Potato starch | 0.010 g |
| Talc | 0.005 g |
| Magnesium stearate | 0.005 g |

EXAMPLE 11

| Coated Tablets | | |
| --- | --- | --- |
| CORE | Derivative n° 9 | 0.075 g |
| | Calcium carbonate | 0.010 g |
| | Magnesium stearate | 0.010 g |
| | Talc | 0.005 g |
| COATING | Gum tragacanth | 0.003 g |
| | Shellac | 0.002 g |
| | Rosin | 0.002 g |
| | Glucose | 0.010 |
| | White wax | 0.001 g |
| | New coccine | traces |
| | Sugar, sufficient for 1 coated tablet | |

EXAMPLE 12

| Capsules | | |
| --- | --- | --- |
| Derivative n° 18 | 0.125 | g |
| Talc | 0.005 | g |
| Magnesium stearate | 0.005 | g |

EXAMPLE 12-continued

| Capsules | | |
|---|---|---|
| Starch | 0.005 | g |

EXAMPLE 13

| Syrup | | |
|---|---|---|
| Derivative n° 22 | 2.00 | g |
| Sweetened and flavoured excipient, sufficient for | 100 | ml |

EXAMPLE 14

| INJECTABLE SOLUTION | | |
|---|---|---|
| Derivative n° 29 | 0.100 | g |
| Isotonic solution, sufficient to make | 2 | ml |

The composition of this invention is usefully administrable for the treatment of the various stages of inflammation. It is applicable in chronic inflammatory rheumatism, degenerative rheumatism, in abarticular conditions, in oto-rhino-laryngology, in stomatology, in post-operative surgery and in traumatology.

In view of its inhibiting effect on blood plate aggregation, it is administrable to patients suffering from disorders of the cerebral and peripheral circulatory system.

Having now described my invention what I claim as new and desire to secure by Letters Patent is:

1. A compound selected from the group consisting of the thieno-pyridine derivatives having the formulae

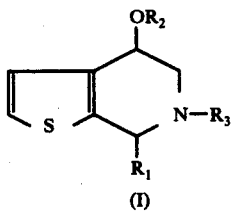

(I)

in which $R_1$ is selected from the group consisting of hydrogen and the alkyl groups having 1-6 carbon atoms; $R_2$ is selected from the group consisting of hydrogen, acetyl and lower alkyl-carbamoyl; and $R_3$ is selected from methyl, nitrobenzyl, chlorobenzyl, methoxybenzyl, chlorobenzoyl, trimethoxybenzoyl, pyrrolidinoacetyl, p.toluene-sulfonyl, phenylcarbamoyl, phenylthiocarbamoyl, 3-oxo-butyl, lower alkyl-carbamoyloxy, phenethyl, dichloroacetyl, 2-chlorophenoxy-2-methyl-propionyl and chlorophenyl-carbamoyl; and the pharmaceutically acceptable acid addition salts thereof.

2. Therapeutic composition having an anti-inflammatory activity and an inhibitor activity on blood plate aggregation, comprising an effective amount of a compound selected from the group consisting of the thieno-pyridine derivatives having the formulae:

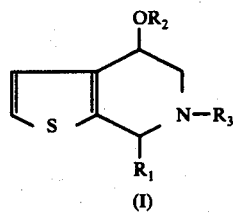

(I)

in which $R_1$ is selected from the group consisting of hydrogen and the alkyl groups having 1-6 carbon atoms; $R_2$ is selected from the group consisting of hydrogen, acetyl and lower alkyl-carbamoyl; and $R_3$ is selected from the group consisting of oxybenzyl, chlorobenzoyl, trimethoxybenzoyl, pyrrolidinoacetyl, p.toluene-sulfonyl, phenylcarbamoyl, phenylthiocarbamoyl, 3-oxo-butyl, lower alkyl-carbamoyloxy, phenethyl, dichloroacetyl, 2-chlorophenoxy-2-methyl-propionyl and chlorophenyl-carbamoyl; and the pharmaceutically acceptable acid addition salts thereof, together with an inert pharmaceutical vehicle.

3. Therapeutic composition as claimed in claim 2, in unit dosage form, each unit dose containing 0.025-0.500 g active ingredient.

4. A thieno-pyridine derivative selected from the group consisting of 7-hydroxy-5-p.nitrobenzyl-4,5,6,7-tetrahydro-thieno[3,2-c]-pyridine, 7-hydroxy-5-(3-oxo-butyl)-4,5,6,7-tetrahydro-thieno[3,2-c]-pyridine, 7-acetoxy-5-o-chlorobenzyl-4,5,6,7-tetrahydro-thieno[3,2-c]-pyridine, 7-hydroxy-5-methyl-4,5,6,7-tetrahydro-thieno[3,2-c]-pyridine, 5-o-chlorobenzyl-7-hydroxy-4,5,6,7-tetrahydro-thieno [3,2-c]-pyridine, 7-hydroxy-5-o-nitrobenzyl-4,5,6,7-tetrahydro-thieno[3,2-c]-pyridine, and the pharmaceutically acceptable acid addition salts thereof.

* * * * *